US009720132B2

(12) United States Patent
Krökel et al.

(10) Patent No.: US 9,720,132 B2
(45) Date of Patent: Aug. 1, 2017

(54) ILLUMINATION FOR THE DETECTION OF RAINDROPS ON A WINDOW BY MEANS OF A CAMERA

(71) Applicant: Conti Temic microelectronic GmbH, Nürnberg (DE)

(72) Inventors: Dieter Krökel, Eriskirch (DE); Wolfgang Fey, Bodolz (DE); Martin Randler, Immenstaad (DE)

(73) Assignee: Conti Temic microelectronic GmbH, Nürnberg (DE)

( * ) Notice: Subject to any disclaimer, the term of this patent is extended or adjusted under 35 U.S.C. 154(b) by 107 days.

(21) Appl. No.: 14/437,632

(22) PCT Filed: Dec. 19, 2013

(86) PCT No.: PCT/DE2013/200377
§ 371 (c)(1),
(2) Date: Apr. 22, 2015

(87) PCT Pub. No.: WO2014/108123
PCT Pub. Date: Jul. 17, 2014

(65) Prior Publication Data
US 2015/0276982 A1    Oct. 1, 2015

(30) Foreign Application Priority Data

Jan. 11, 2013  (DE) .................. 10 2013 100 292

(51) Int. Cl.
*G01W 1/14*    (2006.01)
*G01N 21/43*   (2006.01)
(Continued)

(52) U.S. Cl.
CPC .............. *G01W 1/14* (2013.01); *G01N 21/17* (2013.01); *G01N 21/43* (2013.01); *B60S 1/0844* (2013.01); *G01N 2021/435* (2013.01)

(58) Field of Classification Search
CPC ........... B60R 1/00; B60R 11/04; G01N 21/55; G01W 1/14
(Continued)

(56) References Cited

U.S. PATENT DOCUMENTS 6,365,908 B1 *  4/2002  Waigel .................. G08B 19/02
                                              250/227.25
6,555,804 B1    4/2003  Blasing
(Continued)

FOREIGN PATENT DOCUMENTS

DE    102005000650    7/2006
DE    102008044003    5/2010
(Continued)

OTHER PUBLICATIONS

International Preliminary Report on Patentability for International Application No. PCT/DE2013/200377 issued Jul. 14, 2015.
(Continued)

*Primary Examiner* — Seung C Sohn
(74) *Attorney, Agent, or Firm* — RatnerPrestia

(57) ABSTRACT

A device for detecting rain includes a camera and a lighting source for emitting visible light onto a window. The camera and the lighting source are configured and arranged in such a way that the camera can detect a signal of the visible light which the lighting source emits onto the window. The signal which is detected by the camera correlates with visible light of the lighting source, which visible light is reflected or scattered at the inner face of the window or outer face of the window and/or at the raindrop. The visible light passes through a shutter device which causes the light to be blocked or highly attenuated in a predefined direction perpendicular to the illumination direction of structures of the shutter device. In contrast, the light in the direction perpendicular to
(Continued)

the predefined direction and to the illumination direction can propagate virtually unimpeded through the shutter device.

11 Claims, 3 Drawing Sheets

(51) Int. Cl.
 *G01N 21/17* (2006.01)
 *B60S 1/08* (2006.01)
(58) Field of Classification Search
 USPC .......................................... 250/227, 29, 25
 See application file for complete search history.

(56) References Cited

U.S. PATENT DOCUMENTS

| | | | |
|---|---|---|---|
| 6,831,288 B1 * | 12/2004 | Schmitt | B60Q 1/1423 250/227.25 |
| 7,259,367 B2 | 8/2007 | Reime | |
| 7,579,940 B2 * | 8/2009 | Schofield | B60C 23/00 340/425.5 |
| 7,583,184 B2 * | 9/2009 | Schofield | B60C 23/00 340/425.5 |
| 8,362,453 B2 * | 1/2013 | Taoka | B60S 1/0844 250/227.25 |
| 2009/0128629 A1 | 5/2009 | Egbert | |
| 2011/0204206 A1 * | 8/2011 | Taoka | B60S 1/0844 250/208.1 |
| 2012/0026318 A1 | 2/2012 | Huelsen | |
| 2013/0235381 A1 | 9/2013 | Kroekel | |
| 2014/0300738 A1 | 10/2014 | Mueller | |

FOREIGN PATENT DOCUMENTS

| | | |
|---|---|---|
| DE | 102009000003 | 7/2010 |
| DE | 102011103302 | 12/2012 |
| EP | 1580092 | 9/2005 |
| EP | 2062777 | 5/2009 |
| WO | 2012092911 | 7/2012 |
| WO | 2013091619 | 6/2013 |

OTHER PUBLICATIONS

German Search Report for German Application No. DE 10 2013 100 292.7 mailed Sep. 19, 2013.
International Search Report for International Application No. PCT/DE2013/200377 mailed Jun. 13, 2014.

* cited by examiner

ILLUMINATION FOR THE DETECTION OF RAINDROPS ON A WINDOW BY MEANS OF A CAMERA

CROSS REFERENCE TO RELATED APPLICATIONS

This application is the U.S. National Phase Application of PCT International Application No. PCT/DE2013/200377, filed Dec. 19, 2013, which claims priority to German Patent Application No. 10 2013 100 292.7, filed Jan. 11, 2013, the contents of such applications being incorporated by reference herein.

FIELD OF THE INVENTION

The invention relates to a device for detecting rain on a window by means of a lighting source and a camera.

BACKGROUND OF THE INVENTION

In U.S. Pat. No. 7,259,367 B2, which is incorporated by reference, rain sensing by means of a camera is proposed, said rain sensing providing extensive lighting of the passing-through window of the camera aperture angle with the pane by means of an infrared diode. The camera focus is set to almost infinite and can thus be simultaneously used for driver assistance applications. Due to the imaging on the remote range raindrops are only noticeable as disturbances in the image, which are detected by complex differential measurements of the images recorded with infrared light pulsed or modulated in synchronization with the pixel clock.

A device and a method for detecting rain are described in WO 2012/092911 A1, which is incorporated by reference herein. A camera is disposed behind a pane, in particular in the interior of a vehicle behind a windshield, and focused onto a remote region that lies in front of the pane. A lighting source for generating at least one light beam that is directed at the pane directs the at least one light beam towards the window such that at least one beam that is reflected from the outer face of the pane impinges on the camera as an external light reflex or external reflex. The light quantity of the at least one beam or light reflex that impinges on the camera can be measured by the camera. The lighting source can generate light in the visible wavelength range. It must be ensured that road users are not disturbed by the lighting. To this end, the intensity and duration of the lighting can be adjusted to the external brightness.

However, lighting with visible light, even if it complies with the lighting guidelines for vehicles, can be deemed to be annoying. Other road users, in particular pedestrians, could be disturbed by such lighting, if they notice it.

SUMMARY OF THE INVENTION

An aspect of this invention is to overcome the indicated difficulties of the devices known from the prior art and to indicate optimized lighting for camera-based rain detection.

An aspect of the invention is based on the following basic considerations: the advantage of lighting in the visible wavelength range is that standard driver assistance cameras with color resolution can fully detect this spectral range while, in contrast, infrared light does not, as a rule, pass the standard infrared blocking filter for optimized color resolution and cannot therefore be detected by these driver assistance cameras. In the case of a lighting geometry where the lighting generates light in a wide beam angle, the light-emitting surface is visible particularly laterally due to the wide beam angle. Other road users, e.g. pedestrians, located at the side of a vehicle at the level of the windshield, may be irritated by this.

A device for detecting rain according to an aspect of the invention comprises a camera and a lighting source for emitting visible light onto a window. The camera and the lighting source are configured and arranged in such a way that the camera can detect a signal of the visible light which the lighting source emits onto the window. In particular, in this context the signal which is detected by the camera correlates with visible light of the lighting source, which visible light is reflected or scattered at the inner face of the window or outer face of the window and/or at the raindrop.

The visible light passes through a shutter device which causes the light to be blocked or highly attenuated in a predefined direction perpendicular to the illumination direction of structures of the shutter device. High attenuation exists, in particular, when a maximum of 10% of the light quantity can propagate in the direction blocked off without a shutter device. In contrast, the light in the direction perpendicular to the predefined direction and to the illumination direction can propagate virtually unimpeded through the shutter device. The shutter device preferably acts like a blind. It allows the light to pass through very well in a predefined direction, while the light is blocked by slats of the blind transversely to this direction.

In other words, the shutter device is arranged between the lighting source and the outer face of the window and produces the effect explained above, namely that the propagation of the light is reduced or prevented in a predefined transverse direction and, indeed, preferably towards both sides in this transverse direction (i.e. in the positive and negative directions).

The advantage of this is that the direction in which the visible light of the lighting source can escape from the window can be controlled and therefore it is possible to avoid adversely affecting objects and persons which are located outside the window (e.g. at the sides).

The camera preferably comprises an image sensor, for example a CCD or CMOS sensor, and a lens or imaging system for focusing electromagnetic radiation from one or more areas onto the image sensor.

The lighting source can be configured as one or more light-emitting diodes (LEDs) or as a light band. Advantageously, the lighting source generates flat lighting.

Rain is preferably detected on the outer face of the window in that the camera is arranged behind the window and is focused onto a remote region in front of the window.

Advantageously, at least one light beam is generated by the lighting source and is directed towards the window such that at least one beam that is reflected from the outer face of the window impinges on the camera.

The light reflex(es) of the at least one beam that is reflected from the outer face of the window is/are preferably measured by means of the camera and the measured light reflex(es) of the at least one beam that is reflected from the outer face of the window is/are evaluated in order to detect rain on the outer face of the window.

According to an advantageous embodiment the window is the windshield of a vehicle and the predefined (blocking) direction is perpendicular to the illumination direction and perpendicular to the longitudinal direction of the vehicle or corresponds to the transverse direction of the vehicle. In this way it is possible to avoid dazzling or irritating other road users, in particular pedestrians, located at the side of the vehicle at the level of the windshield.

In a preferred embodiment the shutter device is or comprises a grille which comprises slats as structures.

Advantageously, the camera comprises a view funnel or a view shield or a lens hood, which particularly restricts the field of vision of the camera (downwards) and ideally minimizes stray and scattered light reflexes. The shutter device is arranged on the view funnel or is integrated into the view funnel. In order to achieve a compact design of the camera with integrated lighting, the lighting source can preferably be arranged below the view funnel. To allow the light from the lighting source to impinge on the window, the view funnel is preferably designed to be permeable to visible light in the area through which the light beam passes from the lighting source to the window. For this purpose, the shutter device can advantageously be integrated into the view funnel in such a way that it "replaces" the view funnel in this area. Alternatively, the view funnel can have an area made of material which is permeable to light and the shutter device can, for example, be arranged above or below it.

The structures of the shutter device are preferably arranged parallel to each other, wherein they can additionally be identical distances from one another (arranged equidistantly).

In an alternative advantageous embodiment the structures of the shutter device, which is arranged in or on the view funnel, can be arranged so that they are adapted to the geometry of the surface of the view funnel. The surface of a view funnel is generally not rectangular but symmetrically trapezoidal. The structures cannot therefore be advantageously arranged exactly parallel, but in such a way that they divide the view funnel in the viewing direction into areas or paths of equal size.

Adjacent structures of the shutter device can preferably be a distance of less than 100 μm apart, i.e. in the micrometer range. Grilles with this structure size (slat width e.g. approx. 15 μm) already exist, e.g. as privacy filters for computer displays; they can advantageously be produced as thin films.

Alternatively, adjacent structures of the shutter device can advantageously be a distance in the range of 0.1 mm to 1 mm, i.e. in the millimeter range, apart. The advantage of larger structures is that they can be produced with the aid of injection molding technology. The manufacture of the grille can even advantageously be combined with the manufacturing process for a light guide, which can also be manufactured using injection molding technology, in a two-component injection molding method.

The required height of the grille or the shutter device results from simple geometrical considerations regarding the structure width and slat height. Thus, for example, at a ratio of structure width to slat height of 1:1 with infinitely thin slats having an absorption coefficient of 1, the lateral beam angle transversely to the slat structure would be restricted to 45°. This lateral beam restriction is already totally sufficient for the intended purpose of suppressing optical disturbances.

The height of the structures is therefore advantageously approximately equal to the distance between the structures of the shutter device.

According to an advantageous embodiment the shutter device is configured in such a way that the distance between adjacent structures or the width of the individual structures varies periodically. As a result, a spatial modulation of the lighting is achieved.

In a preferred embodiment a light guide is arranged on the lighting source.

BRIEF DESCRIPTION OF THE DRAWINGS

The shutter device is then advantageously arranged on the light guide.

The invention will be explained in more detail below by means of figures and embodiment examples, where.

DETAILED DESCRIPTION OF THE PREFERRED EMBODIMENTS

Figure 1:
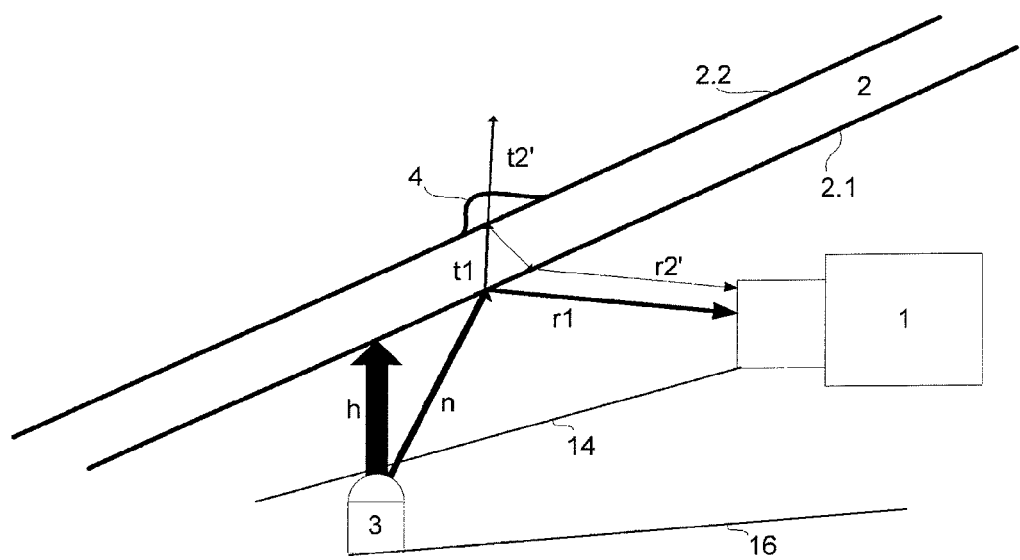
FIG. 1 schematically shows the basic principle of a possible arrangement of the lighting source and camera with beam paths in the event of rain on the window (longitudinal section)

FIG. 1 shows a longitudinal section of a camera (1) focused on the remote region and a lighting source (3) which emits light (h, n) in the visible wavelength range onto a window (2). The beam paths (h, n, t1, r1, t2', r2') explained below are shown schematically. No reflex from the lighting main beam (h) reaches the camera (1). The aperture angle of the lighting is so large that beams reflected from a secondary beam (n) on the inner face (2.1) and outer face (2.2) of the window impinge on the lens or the camera (1) as two spatially separated beams (r1, r2'). Due to the focusing on the remote region, the boundary of the beam bundle is only shown as a blurred image on the image chip (5). Both beams (r1, r2') are sufficiently separated and their respective light reflexes can be measured with the image sensor (5).

The portion (r1) of the secondary beam (n) reflected at the air-window interface (or inner face of the window (2.1)) can serve as a reference beam. Of the portion which is transmitted (t1) into the window, that portion is used as a measurement beam (r2') which is reflected at the window-raindrop interface (or outer face of the window (2.2) and impinges on the camera (1). Not shown is that portion of the beam which is repeatedly reflected inside the window (2) (on the window-air inner face (2.1) after having been reflected at the window-raindrops outer face (2.2)).

If, as shown here, in the event of rain (4), the outer face (2.2) of the windshield (2) is wetted, the majority (t2') of the light transmitted (t1) through the inner face (2.1) into the window is decoupled, so that the reflected portion (r2') is weaker than it is in the case of a dry window (not shown). The beam (r1) reflected from the inner face (2.1) is unaffected by wetting of the outer face of the window (2.2).

By comparing the measured light reflexes of both beams (r1 to r2'), the reduced signal (r2') in the event of rain (4) can easily be measured and a windshield wiper can be activated accordingly.

In this arrangement, the lighting source (3) having a wide beam angle can be integrated into the camera (1), more precisely into the camera housing, e.g. located as shown on a circuit board (16) of the camera system.

The lighting source (3) is arranged here below a view shield or a view funnel (14). The view funnel (14) is permeable to visible light in the region through which the light beam (n) passes from the lighting source (3) to the window (2).

If there are one or more raindrops (4) on the outer face (2.2) of the window (2), the raindrop(s) (4) cause(s) a stronger decoupling (t2') of light from the window in the area in front of the window. As a result, a reduced intensity of the partial beam (r2'), which was reflected at the outer face (2.2) of the window (2), is measured by the camera (1).

Since the lighting source (3) generates visible light (h, n) in a wide beam angle, the light-emitting surface is visible particularly laterally due to the wide beam angle, i.e. perpendicular to the longitudinal sectional plane of FIG. 1. This can irritate other road users, for example pedestrians, located on the side of a vehicle at the height of the (windshield) pane.

Figure 2:
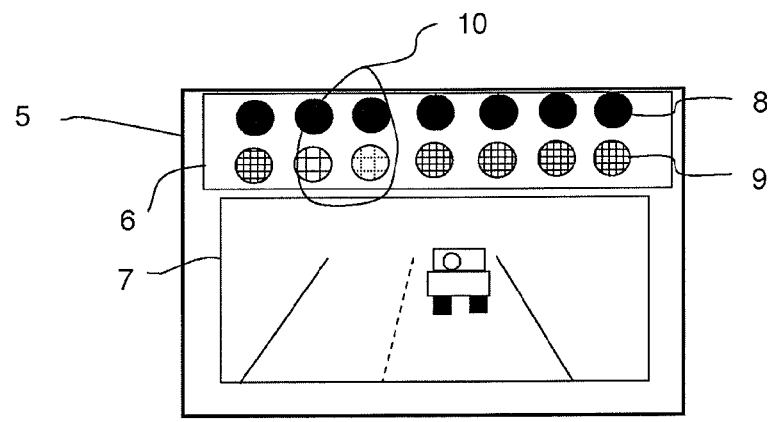
FIG. 2 shows signals detected by an image sensor of a camera, which suggest rain.

FIG. 2 shows in the upper part (6) of the image sensor (5), which serves for rain detection, seven pairs of lighting reflexes (8, 9) each, which are e.g. generated by seven LEDs as the lighting source (3). These are not shown as sharp images but are noticeable, due to the focus of the camera (1) being set to infinite. In particular, the light intensity or quantity can be measured. The upper lighting reflexes (8) are generated by beams (r1) reflected at the inner face (2.1) of the windshield (2), the lower lighting reflexes (9) are generated by beams (r2') reflected at the outer face (2.2) of the windshield.

FIG. 2 thus shows an exemplary proportioning of the driver assistance area (7) and the rain sensor area (6) on the image chip (5). Both areas detect light (electromagnetic radiation) in the visible wavelength range and typically overlap in the rain sensor area (6). The lighting reflexes from the outer windshield (9), above which lies a raindrop (4), are attenuated in intensity. These lighting reflexes (9) originate from beams (r2') reflected at the outer face (2.2) of the windshield (2) and are of reduced intensity (10), since the majority of the beam transmitted (t1) into the windshield (2) is decoupled (t2') from the windscreen by raindrops (4) and thus is not reflected (r2') back to the camera (1). Consequently, these lighting reflexes (9) carry in them the information whether there is rain (4) on the outer face (2.2) of the window (2), and their light quantity or distribution pattern could be used alone as a measurement signal.

Figure 3:
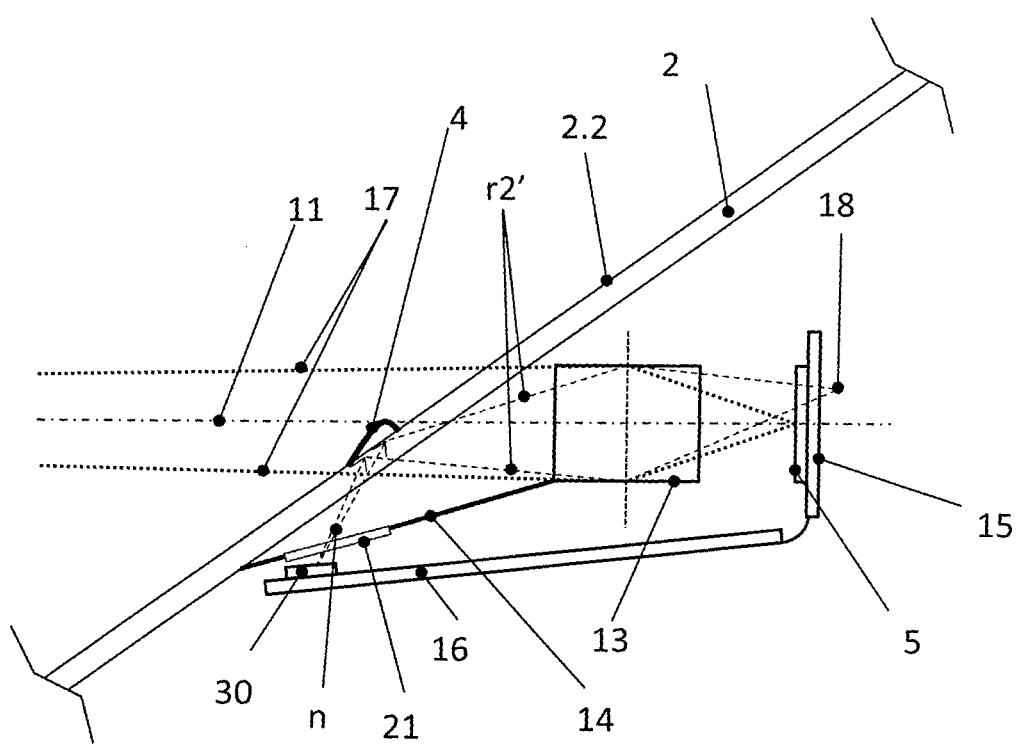
FIG. 3 shows a camera with an LED for lighting (longitudinal section)

One embodiment example of the invention is shown as a longitudinal section in FIG. 3. The basic arrangement and design of the lighting source (3), window (2) and camera (1) correspond to the arrangement shown in FIG. 1. The camera (1) shown here comprises an image sensor (5), two circuit boards (15, 16), a lens or imaging system (13) and a view funnel (14). The image sensor (5) is arranged on a first circuit board (15) which is connected to a second circuit board (16). The view funnel (14) limits the field of vision of the camera (1).

The schematic diagram of FIG. 3 shows how the remote region is imaged by the imaging system (13) or lens in a focused manner on the image sensor (5) of the camera (1). The beam path of the remote region imaging (17) is shown schematically by dotted lines. The beam path (n, r2') of the lighting or close-range imaging is shown schematically by dashed lines. The focal point (18) of the imaging of the lighting beams (r2') reflected on the outer face (2.2) of the window is located behind the image sensor (5). Therefore, these lighting reflexes (9) are out of focus in the camera image.

In this embodiment example, a plurality of light-emitting diodes (LEDs) (30) which are arranged in a row on the second circuit board (16) are used as the lighting source (3). A grille is mounted in front of the LEDs (30) as a shutter device (20). The grille is in this case integrated into the view funnel (14). The slats (21) of the grille (20) are configured and arranged in such a way that no light or only a little light can escape from the LEDs (30) perpendicular to the plane which corresponds to the longitudinal section shown, from the camera (1) or from the window (2). To this end, the grille slats (21) may be arranged, for example, parallel to the optical axis (11) of the camera (1) which is shown by a dotdashed line.

Figure 4:
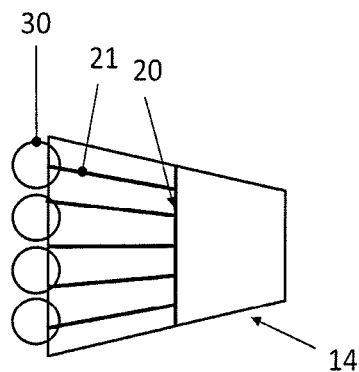
FIG. 4 shows a top view of the view funnel with four LEDs arranged below it in series.

FIG. 4 shows a top view of a view funnel (14) with four LEDS (30) arranged below it, which are arranged in a row. Here, too, a grille is provided as a shutter device (20), said grille being integrated into the view funnel (14). Slats are in turn provided as blind structures (21), which are not, however, arranged so that they are aligned exactly parallel to one another or to the optical axis, but which are adapted to the geometry of the surface of the view funnel (14). This slat arrangement also causes the light to be blocked perpendicularly to the optical axis (11), i.e. upwards and downwards in FIG. 4, by the slats (21) of the grille (20). In contrast, the grille slats (21) allow the visible light (n) generated by the LEDs (30) to pass through the view funnel (14) onto the window (2).

Figure 5:
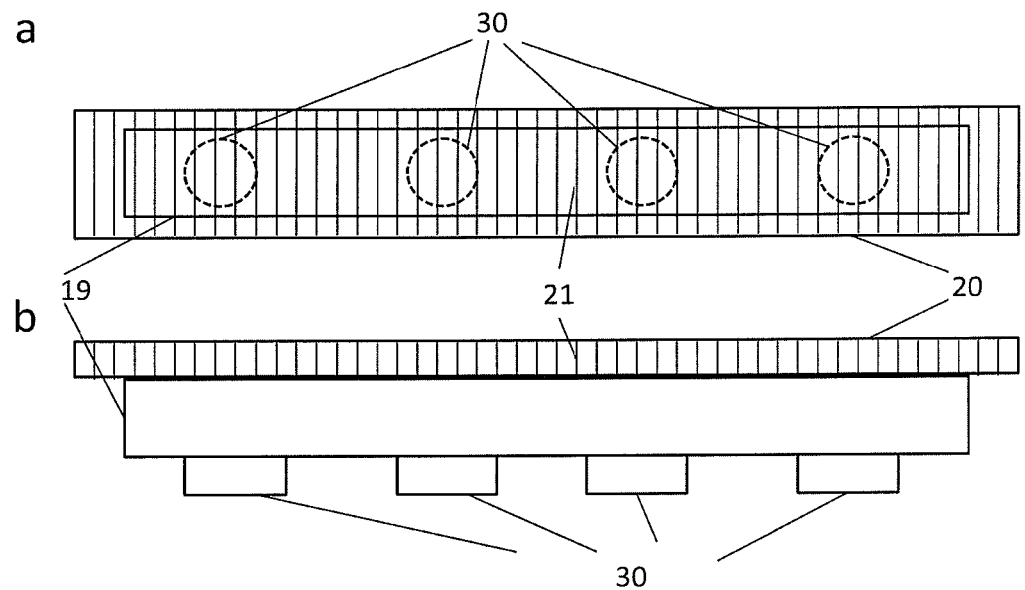
FIG. 5 shows a grille, a light guide and LEDs in a top view and in cross-section.

FIG. 5 finally shows an alternative embodiment of a lighting source (3) with light-emitting diodes (30), a light guide (19) and grille (20). FIG. 5a shows the top view and FIG. 5b shows the transverse section of this arrangement. A light guide (19) is arranged on the four adjacent light-emitting diodes (30). The grille is located on the light guide as a blind structure (20). The slats (21) of the grille (20) are arranged parallel to one another and are preferably aligned parallel to the optical axis (11) of the camera (1).

The slats (21) or the grille (20) can be produced, for example, by means of injection molding technology. The manufacture of the grille (20) can even be advantageously combined with the manufacturing process for the light guide (19), which can also be manufactured using injection molding technology, in a two-component injection molding method.

LIST OF REFERENCE NUMERALS

1 Camera
2 Window
2.1 Inner face of the window
2.2 Outer face of the window
3 Lighting source
4 Rain, raindrops
5 Image sensor
6 Rain sensor area
7 Driver assistance area
8 Lighting reflex from window inner face
9 Lighting reflex from window outer face
10 Signal change in the event of raindrops
11 Optical axis
13 Imaging system or lens
14 View funnel
15 First circuit board
16 Second circuit board
17 Remote region beam path (vehicle surroundings)
18 Focal point of close range imaging (window outer face)
19 Light guide
20 Shutter device or grille
21 Shutter device structures or grille slats
30 LED
H Lighting main beam
N Lighting secondary beam or beam path
R1 Portion of n which is reflected at the window inner face
t1 Portion of n which is transmitted at the window inner face
r2' Portion of t1 which is reflected at the window outer face in the event of rain
t2' Portion of t1 which is transmitted at the window outer face in the event of rain

The invention claimed is:

1. A device for detecting rain on a window of a vehicle, the device comprising:
   a camera;
   a lighting source for emitting visible light in an illumination direction onto a window of the vehicle; and
   a shutter device having a grille with a plurality of slats between the lighting source and the window, the slats directing the visible light in the illumination direction onto the window while blocking or attenuating the visible light in directions other than the illumination direction,
   wherein the camera and the lighting source are configured and arranged in such a way that the camera can detect the visible light which the lighting source emits onto the window.

2. The device according to claim 1, wherein the window is the windshield of a vehicle and wherein the predefined direction is perpendicular to the illumination direction and perpendicular to the longitudinal direction of the vehicle.

3. The device according to claim 1, further comprising a view funnel, wherein the shutter device is arranged on the view funnel or is integrated into the view funnel.

4. The device according to claim 3, wherein the structures of the shutter device are arranged so that they are adapted to the geometry of the surface of the view funnel.

5. The device according to claim 1, wherein the structures of the shutter device are arranged parallel to one another.

6. The device according to claim 1, wherein adjacent structures of the shutter device are arranged at a distance of less than 100 μm apart.

7. The device according to claim 1, wherein adjacent structures of the shutter device are arranged at a distance in the range of 0.1 mm to 1 mm apart.

8. The device according to claim 1, wherein the height of the structures is approximately equal to the distance between the structures of the shutter device.

9. The device according to claim 1, wherein the shutter device is configured in such a way that the distance between adjacent structures and/or the width of the structures varies periodically.

10. The device according to claim 1, wherein a light guide is arranged on the lighting source.

11. The device according to claim 10, wherein the shutter device is arranged on the light guide.

* * * * *